(12) United States Patent
Schuhmann et al.

(10) Patent No.: US 9,982,167 B2
(45) Date of Patent: May 29, 2018

(54) PRECURSOR COMPOSITE MATERIAL, METHOD FOR PRODUCING A PRECURSOR COMPOSITE MATERIAL, METHOD FOR PRODUCING A COMPOSITE MATERIAL AND USE OF A PRECURSOR COMPOSITE MATERIAL AND OF A COMPOSITE MATERIAL

(71) Applicant: INFIANA GERMANY GMBH & CO. KG, Forchheim (DE)

(72) Inventors: Michael Schuhmann, Grosshabersdorf (DE); Christian Hermann, Eggolsheim (DE)

(73) Assignee: INFIANA GERMANY GMBH & CO. KG (DE)

( * ) Notice: Subject to any disclaimer, the term of this patent is extended or adjusted under 35 U.S.C. 154(b) by 0 days. days.

(21) Appl. No.: 15/101,868

(22) PCT Filed: Nov. 17, 2014

(86) PCT No.: PCT/EP2014/074771
§ 371 (c)(1),
(2) Date: Jun. 3, 2016

(87) PCT Pub. No.: WO2015/082200
PCT Pub. Date: Jun. 11, 2015

(65) Prior Publication Data
US 2016/0369132 A1   Dec. 22, 2016

(30) Foreign Application Priority Data
Dec. 5, 2013   (DE) .................. 10 2013 113 532

(51) Int. Cl.
*C09J 7/02*       (2006.01)
*A61L 15/22*      (2006.01)
(Continued)

(52) U.S. Cl.
CPC .......... *C09J 7/0275* (2013.01); *A61F 13/5605* (2013.01); *A61F 13/60* (2013.01);
(Continued)

(58) Field of Classification Search
CPC ........... B32B 7/06; B32B 27/32; B32B 27/34; B32B 27/36; B32B 27/302; B32B 27/08;
(Continued)

(56) References Cited

U.S. PATENT DOCUMENTS 2,746,893 A * 5/1956 Matthes .................... B44C 1/17
                                                    428/202
4,331,727 A    5/1982 Maas
(Continued)

FOREIGN PATENT DOCUMENTS

DE    100 21 109 A1    11/2001
DE    102 46 864 A1    4/2004
(Continued)

OTHER PUBLICATIONS

English translation International Search Report corresponding to PCT/EP2014/074771 dated Feb. 5, 2015; 2 pages.
(Continued)

*Primary Examiner* — Patricia L. Nordmeyer
(74) *Attorney, Agent, or Firm* — Mintz Levin Cohn Ferris Glovsky and Popeo P.C.

(57) ABSTRACT

A precursor composite material (60) is provided, having a layer sequence (50) comprising an adhesive layer (20), a carrier layer (10) on the adhesive layer (20), a release layer (40) on the carrier layer (10) and a parting layer (30) on the release layer (40), wherein the layer sequence (50) is arranged in such a way that the side of the adhesive layer (20) facing away from the layer sequence (50) is arranged at least in sub-regions on the side of the parting layer (30) facing away from the layer sequence (50). Further provided
(Continued)

Figure 2:
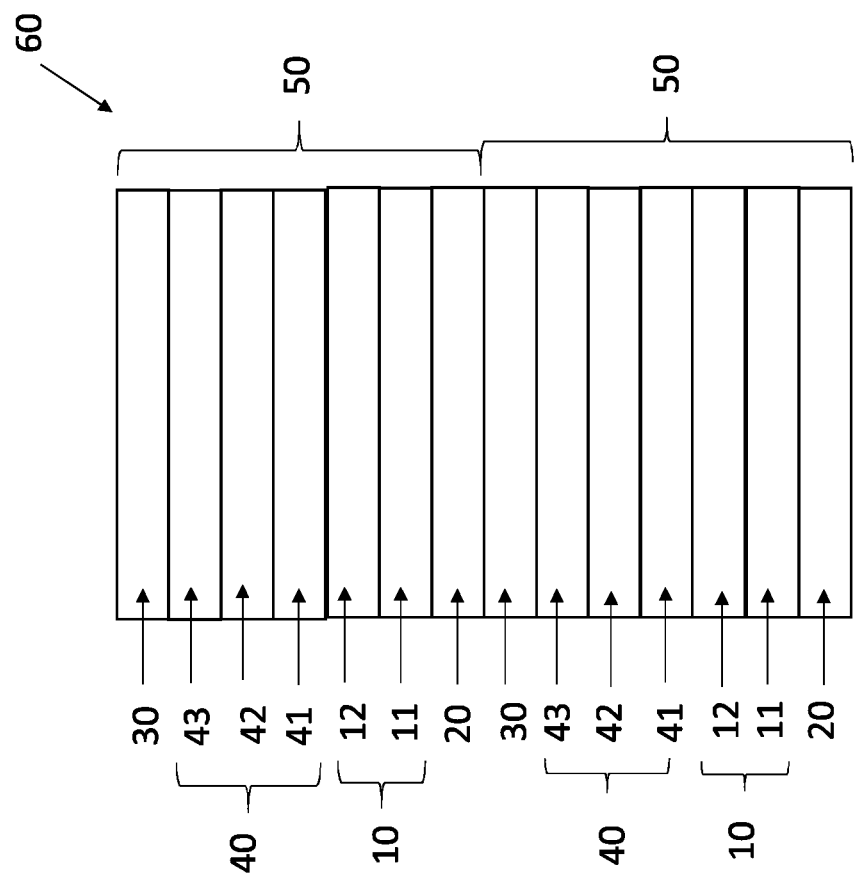

are a composite material, a method for producing the precursor composite material, a method for producing the composite material and a use of the precursor composite material and of the composite material.

12 Claims, 11 Drawing Sheets

(51) Int. Cl.
    *A61F 13/56*     (2006.01)
    *A61F 13/60*     (2006.01)
    *B32B 27/36*     (2006.01)
    *B32B 7/06*     (2006.01)
    *B32B 27/08*     (2006.01)
    *B32B 7/12*     (2006.01)
    *B32B 27/28*     (2006.01)
    *B32B 27/30*     (2006.01)
    *B32B 27/32*     (2006.01)
    *B32B 27/34*     (2006.01)
    *A61L 15/58*     (2006.01)

(52) U.S. Cl.
CPC ........... *A61L 15/225* (2013.01); *A61L 15/585* (2013.01); *B32B 7/06* (2013.01); *B32B 7/12* (2013.01); *B32B 27/08* (2013.01); *B32B 27/283* (2013.01); *B32B 27/302* (2013.01); *B32B 27/32* (2013.01); *B32B 27/34* (2013.01); *B32B 27/36* (2013.01); *C09J 7/243* (2018.01); *C09J 7/29* (2018.01); *B32B 2274/00* (2013.01); *B32B 2307/724* (2013.01); *B32B 2307/748* (2013.01); *B32B 2519/00* (2013.01); *C09J 2423/005* (2013.01); *C09J 2423/006* (2013.01); *C09J 2425/005* (2013.01); *C09J 2467/005* (2013.01); *C09J 2477/005* (2013.01); *C09J 2483/00* (2013.01)

(58) Field of Classification Search
CPC ..... B32B 27/283; B32B 7/12; B32B 2274/00; B32B 2307/724; B32B 2307/748; B32B 2519/00; A61F 13/60; A61F 13/5605; C09J 2477/005; C09J 2467/005; C09J 2425/005; C09J 2483/00; C09J 2423/005; C09J 7/0275; C09J 2423/006; Y10T 428/14; Y10T 428/28; A61L 15/225
See application file for complete search history.

(56) References Cited

U.S. PATENT DOCUMENTS

| | | | | |
|---|---|---|---|---|
| 4,398,985 A * | 8/1983 | Eagon | ............... | C09J 7/0296 156/233 |
| 4,604,153 A * | 8/1986 | Melbye | ............... | B05C 17/06 156/235 |
| 4,767,654 A * | 8/1988 | Riggsbee | ............... | G09F 3/0288 206/390 |
| 4,837,088 A * | 6/1989 | Freedman | ............... | B31D 1/021 156/238 |
| 5,082,706 A | 1/1992 | Tangney | | |
| 5,344,681 A * | 9/1994 | Calhoun | ............... | C09J 7/02 428/202 |
| 5,350,612 A * | 9/1994 | Stern | ............... | B65D 23/14 162/165 |
| 6,372,341 B1 | 4/2002 | Jung et al. | | |
| 6,432,241 B1 * | 8/2002 | Congard | ............... | B65H 19/102 156/157 |
| 6,740,379 B1 | 5/2004 | Congard et al. | | |
| 6,777,053 B1 | 8/2004 | Günter | | |
| 2001/0006713 A1 | 7/2001 | Otten et al. | | |
| 2004/0013838 A1 | 1/2004 | Guenter | | |
| 2004/0109985 A1 | 6/2004 | Furst | | |
| 2006/0127588 A1 | 6/2006 | Muller et al. | | |
| 2008/0191880 A1 | 8/2008 | Tuffe et al. | | |
| 2010/0178824 A1 | 7/2010 | Stark et al. | | |
| 2012/0251757 A1 | 10/2012 | Dalmis et al. | | |

FOREIGN PATENT DOCUMENTS

| | | |
|---|---|---|
| DE | 698 24 274 T2 | 6/2005 |
| DE | 10 2005 046 309 A1 | 4/2007 |
| DE | 10 2006 028 901 A1 | 12/2007 |
| DE | 10 2009 045 812 A1 | 4/2011 |
| EP | 1 113 059 A2 | 7/2001 |
| EP | 1 283 242 A1 | 2/2003 |
| EP | 0 877 052 B1 | 3/2004 |
| EP | 1 661 686 B1 | 5/2006 |
| EP | 1 941 852 B1 | 7/2008 |
| EP | 1 955 965 B1 | 8/2008 |
| EP | 2 256 173 B1 | 12/2010 |
| GB | 2 068 833 A | 8/1981 |
| JP | 01014289 A | 1/1989 |
| RU | 2218376 C2 | 12/2003 |
| WO | 99/25552 A1 | 5/1999 |
| WO | 99/46347 A1 | 9/1999 |
| WO | 00/27621 A2 | 5/2000 |
| WO | 00/30850 A1 | 6/2000 |
| WO | 2011/112387 A2 | 9/2011 |

OTHER PUBLICATIONS

English translation of International Preliminary Report on Patentability (Chapter II) corresponding to PCT/EP2014/074771 recently available on WIPO's PatentScope and dated Mar. 29, 2016; 5 pages; Non-English version included in this submission with mailing date of Nov. 9, 2015; 5 pages.
Russian Office Action for Russian Patent Application No. 2016126602, issued by Russian Federation dated Dec. 11, 2017 in English translation.

* cited by examiner

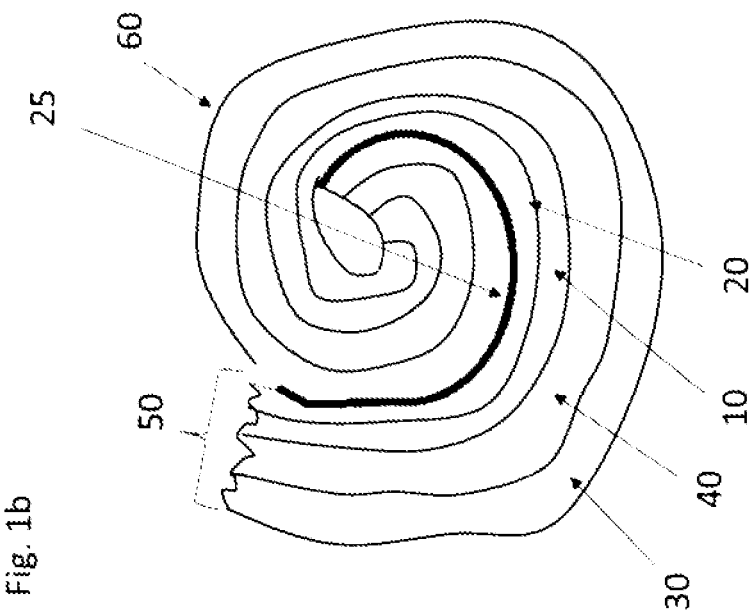
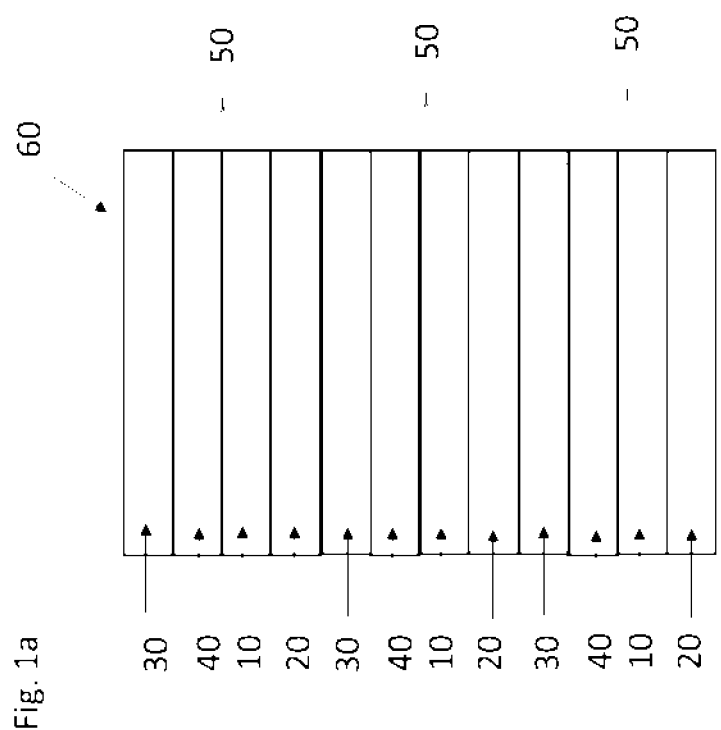

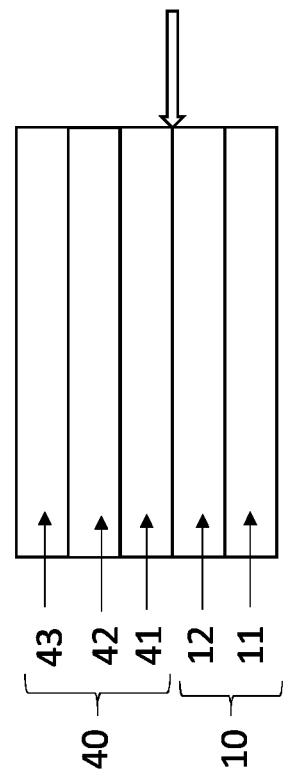
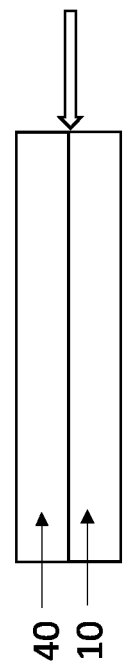
Fig. 4b
Fig. 4a

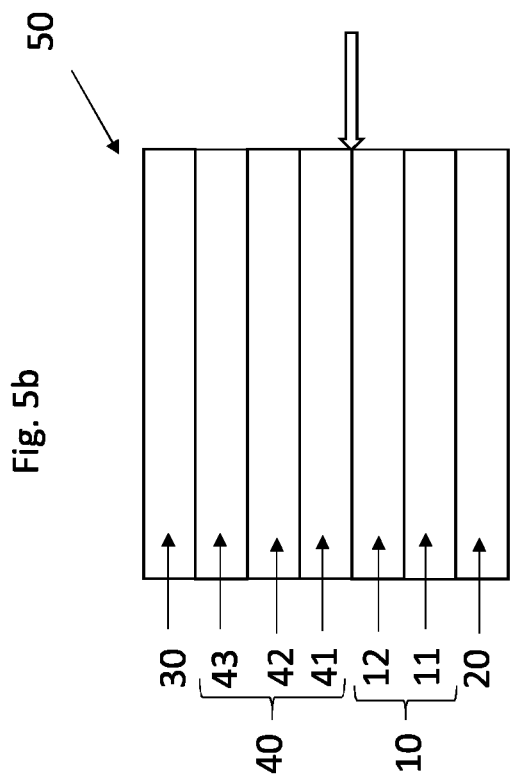
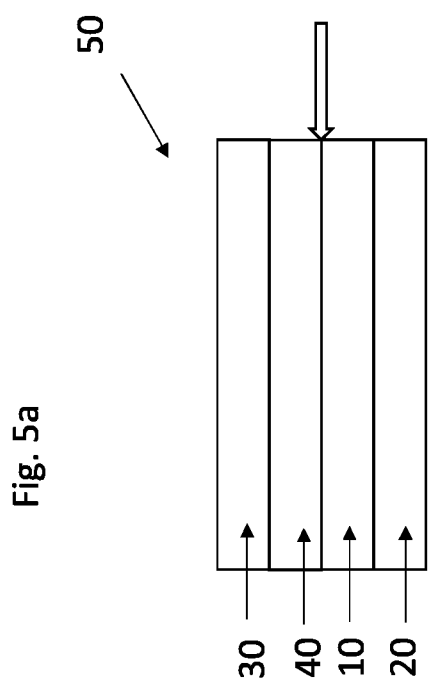

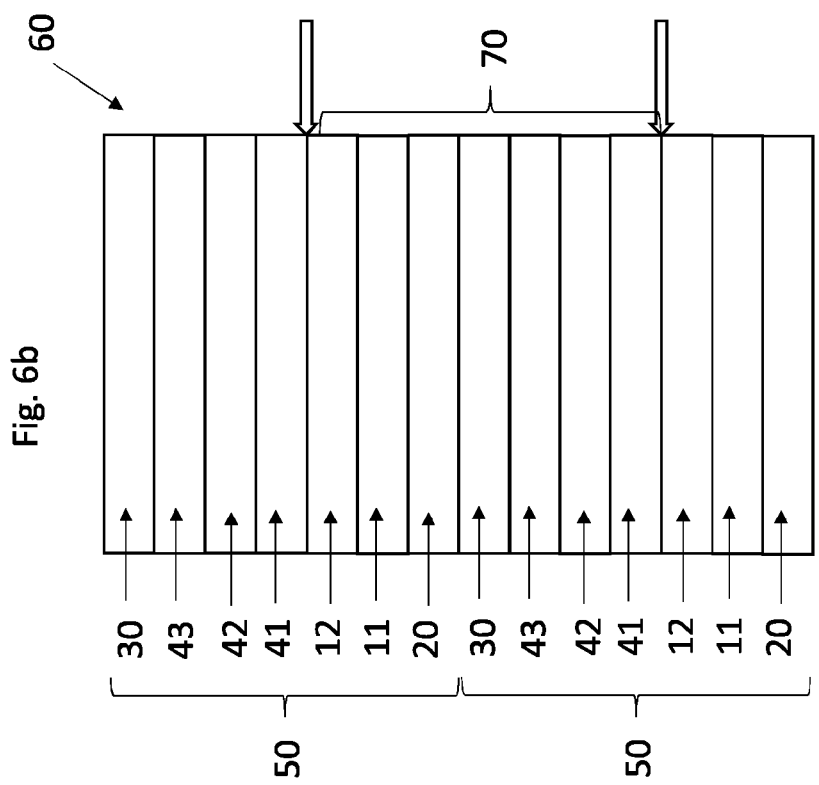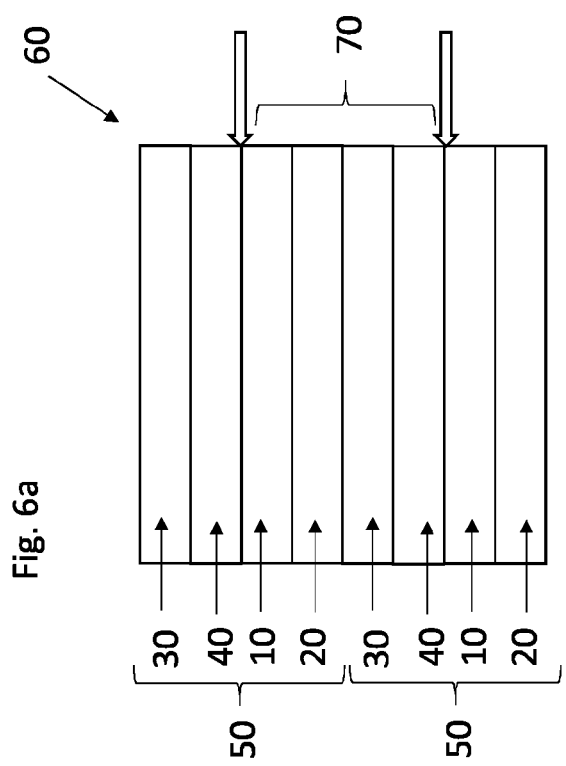

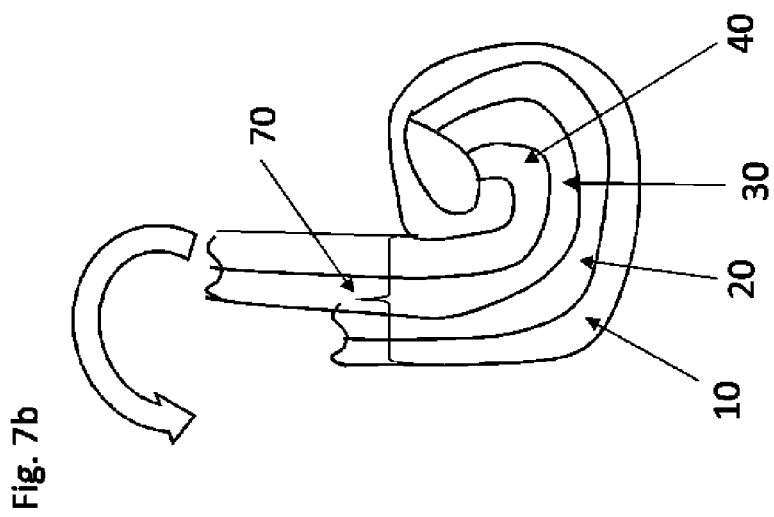
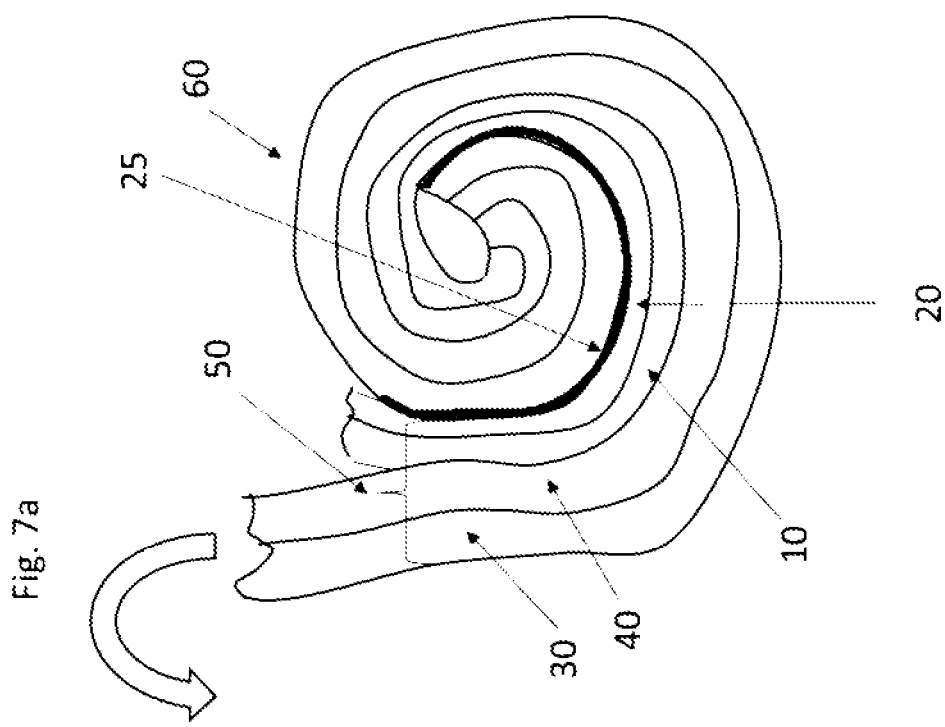

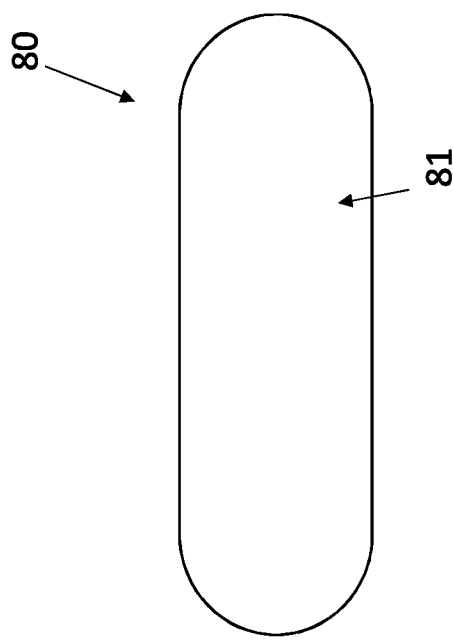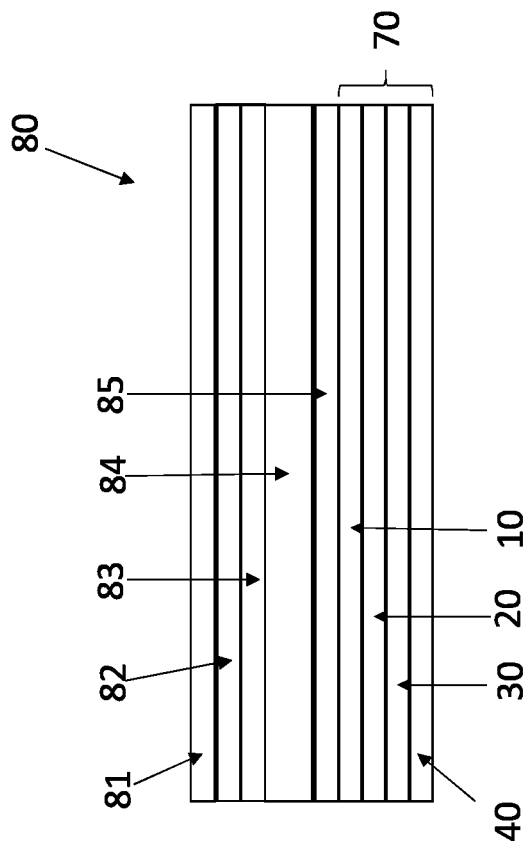

PRECURSOR COMPOSITE MATERIAL, METHOD FOR PRODUCING A PRECURSOR COMPOSITE MATERIAL, METHOD FOR PRODUCING A COMPOSITE MATERIAL AND USE OF A PRECURSOR COMPOSITE MATERIAL AND OF A COMPOSITE MATERIAL

Provided are a precursor composite material, a composite material produced from the precursor composite material, a method for producing the precursor composite material, a method for producing the composite material as well as the use of the precursor composite material and of the composite material.

Composite materials, as used in hygienic laminates or for labels, for example, have previously had the disadvantage that, in order to maintain a certain stability, they are too thick for many uses. In hygienic laminates, such as sanitary towels or pantiliners, for example, this can lead to restricted wearing comfort.

The problem addressed by at least one embodiment of the invention is the provision of a precursor composite material of which a composite material with improved properties can be made, as well as the provision of such a composite material with improved properties. Further problems addressed by further embodiments are the provision of methods for producing a precursor composite material and a composite material with improved properties as well as the use of the precursor composite material for producing the composite materials and the use of the composite material.

A precursor composite material is provided, having a layer sequence comprising an adhesive layer, a carrier layer on the adhesive layer, a release layer on the carrier layer and a parting layer on the release layer, wherein the layer sequence is arranged in such a way that the side of the adhesive layer facing away from the layer sequence is arranged at least in sub-regions on the side of the parting layer facing away from the layer sequence and wherein an adhesive force is present between the adhesive layer and the parting layer, said adhesive force being greater than a delamination force between the carrier layer and the release layer.

"On" with regard to the arrangement of the layers in the layer sequence should be understood as an arrangement of the individual layers in which said individual layers have joint limiting surfaces relative to each other. However, the individual layers of the layer sequence, i.e. adhesive layer, carrier layer, release layer and parting layer can each have partial layers comprising different materials. For example, the carrier layer can have a first carrier layer and a second carrier layer and the release layer a first release layer, a second release layer and a third release layer, and, for example, the first release layer can be arranged on the second carrier layer, i.e. have a joint limiting surface relative to said second carrier layer.

"On" with regard to the arrangement of the layer sequence should also be understood as a direct arrangement, i.e. a joint limiting surface of the side of the adhesive layer facing away from the layer sequence and the side of the parting layer facing away from the layer sequence, at least in sub-regions of the layer sequence.

The precursor composite material thus comprises a layer sequence, having a composite of layers, and thus in turn forming a composite of layer sequences due to the arrangement due to the arrangement of said composite of layers. That means that at least two layer sequences arranged on top of each other are present in a cross-section through the precursor composite material.

The layer sequence of such a precursor composite material has a higher tensile strength than the individual layers of the layer sequence of the precursor composite material. This allows the precursor composite material to be further transformed into a composite material, without damaging any individual or all layers of the layer sequence in the transformation process.

Furthermore, an adhesive force is present between the adhesive layer and the parting layer, said adhesive force being greater than the delamination force between the carrier layer and the release layer. "Delamination" here and in the following should be understood as a releasing force that needs to be applied in order to effect a delamination of the carrier layer from the release layer. When the arrangement of the layer sequence is to be changed, i.e. a wound layer sequence is to be unwound, for example, this allows a delamination, i.e. a separation of the carrier layer from the release layer, to be achieved, while the adhesive layer and the parting layer maintain the joint limiting surface thereof.

This allows a composite material with a layer sequence different to that of the precursor composite material to be simply generated by a precursor composite material arranged as described above. While the precursor composite material is produced with the adhesive layer/carrier layer/release layer/parting layer sequence of layers, delaminating the carrier layer and the release layer allows a composite material with a release layer/parting layer/adhesive layer/carrier layer sequence of layers to be easily obtained. In particular, the selection of the materials of the individual layers of the precursor composite material thus enables a controlled delamination process.

This allows a composite material to be produced by simply re-sorting the layer sequence of the precursor composite material without adding any further materials and/or removing any components present in the precursor composite material. Aside from the sequence of the individual layers in the composite material, the properties of the individual layers of the composite material are thus already determined by the precursor composite material.

The precursor composite material in one embodiment has a layer sequence that is wound. The winding ensures that the side of the adhesive layer facing away from the layer sequence is arranged at least in sub-regions on the side of the parting layer facing away from the layer sequence. In such case, merely the outermost location of the winding has a sub-region of the parting layer or of the adhesive layer, which is free from the respective other layer. In the event of a winding of the layer sequence, at least two layer sequences on top of each other are present inside the winding, depending on the length of the layer sequence.

The release layer can have a thickness of less than 40 µm, preferably less than 30 µm, more preferably less than 20 µm and most preferably less than 15 µm and/or the carrier layer can have a thickness of less than 20 µm, preferably less than 15 µm, more preferably less than 10 µm, most preferably less than 5 µm. For example, the release layer can be less than 100 gsm (gram per m$^2$), preferably less than 50 gsm, more preferably less than 20 gsm, most preferably less than 15 gsm thick. This allows perceptibly thinner release and/or carrier layers than in prior art to be provided. For example, conventional carrier layers have a thickness of 20 to 30 µm and conventional release layers a thickness of approximately 40 µm.

The precursor composite material thus comprises a release layer and/or a carrier layer, which can be designed in a particularly thin manner. However, during the production of the precursor composite material as well as the further transformation thereof into a composite material, the particularly thinly designed release layer and/or carrier layer are never subjected to a tension alone, for example in a production or finishing machine, and can therefore be produced and transformed without destruction. This would not be possible without the presence of the additional layers in the layer sequence of the precursor composite material.

This allows a composite material to be produced from the precursor composite material, which has particularly thin release and/or carrier layers, which in turn leads to advantageous properties when using the composite material. Accordingly, even in the controlled delamination of the carrier layer and of the release layer, the thinnest layer is not subjected alone to a tension alone, and instead only ever in a laminate of layers.

Furthermore, the thickness of the adhesive layer can be less than 50 gsm, preferably less than 30 gsm, preferably less than 15 gsm, particularly preferably less than 5 gsm, for example 2 to 5 gsm. Furthermore, the parting layer can have a thickness of less than 10 gsm, preferably less than 5 gsm, more preferably less than 2 gsm, for example 0.5 to 1 gsm.

Pursuant to one embodiment, the precursor composite material has an adhesive layer, having a material selected from a group comprising pressure-sensitive adhesives. "Pressure-sensitive adhesives" here and in the following should be understood as an adhesive that remains permanently adhesive and/or highly viscous once applied to the carrier layer. The pressure-sensitive adhesive can be selected from a group comprising solvent-containing pressure-sensitive adhesives, pressure-sensitive dispersion adhesives, hot-melt pressure-sensitive adhesives or mixtures thereof. The pressure-sensitive adhesives can be processed on the carrier layer by means of UV radiation and/or thermally. Thus, non-hardening or not completely hardening adhesives, which are pressure-sensitive but do not enter into any chemical bond with the adjacent layers, are selected as material for the adhesive layer.

Furthermore, the release layer of the precursor composite material can have a material selected from a group comprising polyamide, polystyrene, thermoplastic elastomers, polystyrene copolymers, polyester, polyester copolymers, polyolefins and combinations thereof, as well as combinations of the stated materials individually or combinations of the stated materials with adhesion promotors. Examples of thermoplastic elastomers are TPE-E (thermoplastic polyester elastomers or thermoplastic copolyester, for example, Hytrel (DuPont) or Riteflex (Ticona)), TPE-U (urethane-based thermoplastic elastomers, for example Desmopan, Texin, Utechllan (Bayer)), TPE-V (olefin-based crosslinked thermoplastic elastomers, predominantly PP/EPDM, for example Sarlink (DSM), Forprene (SoFter)), TPE-O (olefin-based thermoplastic elastomers, predominantly PP/EDM, for example Santoprene (AES/Monsanto)), TPE-S (styrene block copolymers, such as SBS, SEBS, SEPS, SEEPS and MBS, for example Styroflex (BASF), Septon (Kuraray) or Thermolast (Kraiburg TPE)) and TPE-A (thermoplastic copolyamides, for example PEBAX (Arkema)). Examples of polyolefins are polyethylene or polypropylene. The release layer can be composed of a first, second and third release layer, wherein the first release layer has a material selected from polyethylene, polypropylene, polyamide, thermoplastic elastomers, polystyrene, polystyrene copolymers, polyester, polyester copolymers and combinations thereof, the second release layer is selected from polymer adhesion promotors and the third release layer can have polyolefins, such as polyethylene or polypropylene, for example. Such a combination of release layers can reduce the costs for the release layers, modify the stiffness or softness and improve the punching property of the layer, which can be of relevance for the production of a product in which a composite material produced from the precursor composite material is used.

Furthermore, the precursor composite material can have a carrier layer, having a material selected from a group comprising polyolefins, polyolefin copolymers, thermoplastic elastomers and combinations thereof. Examples of polyolefins are polyethylene and polypropylene. Examples of thermoplastic elastomers are TPE-E, TPE-U, TPE-V, TPE-O, TPE-S and TPE-A. The use of thermoplastic elastomers such as TPE-U and TPE-E is in particular advantageous when a composite material, which has a breathable carrier layer, is to be produced from the precursor composite material. Such carrier layers are, for example, advantageous when the composite material is used in a hygienic laminate.

The carrier layer can, for example, be composed of two layers, wherein the first carrier layer can have a material selected from polyethylene, polypropylene, polypropylene copolymers, thermoplastic elastomers as well as combinations thereof. The second carrier layer can have a material selected from a group comprising polyethylene, polypropylene, polypropylene copolymers, thermoplastic elastomers as well as mixtures thereof.

When selecting the materials for the carrier layer and the release layer, care should be taken to ensure that no boundary phase diffusion occurs between the selected materials and that the materials are thus good for laminating. To this end, at least 50% of the materials in the carrier layer can differ from the materials in the release layer or at least 50% of the materials in the release layer can differ from the materials in the carrier layer. For example, the differing materials in the carrier layer and the release layer can be selected from a polyolefin, for example polyethylene, and polystyrene, a polyolefin, for example polyethylene, and a thermoplastic elastomer, such as TPE-E, a polyolefin and a polyamide, a polyester and a polyolefin, or a low-density polyethylene and polypropylene homopolymer.

Furthermore, the carrier layer can have a precursor composite material can have a material selected from a group comprising silicone, hardened polysiloxane and thermoplastic silicone elastomer. These compounds do not form any bond with the adhesive layer, and therefore said adhesive layer is protected, but the parting layer remains inert. For example, this allows the parting layer to be removed from the adhesive layer in a later product in which a composite material is produced from the precursor composite material.

A composite material is furthermore provided that is produced from a precursor material as outlined above and comprises a release layer, a parting layer on the release layer, an adhesive layer on the parting layer and a carrier layer on the adhesive layer.

The features indicated with regard to the precursor composite material and relating to the release layer, the parting layer, the adhesive layer and the carrier layer also apply accordingly to the composite material. Said composite material thus has an arrangement of layers in which a carrier layer and/or a release layer are present, which can be designed in a particularly thin manner. Compared with conventional composite materials, the release layer can continue not to be produced from paper, but instead of a film made, for example, of polyamide, polystyrene, thermoplastic elastomers, polystyrene copolymers, polyester, polyester copolymers, polyolefins, combinations thereof, as well as combinations of such materials with adhesion promoters. This allows the composite material to be used, for example, in hygienic laminates and contributes therein towards improved wearing comfort or better handling. Furthermore, such a composite material can be used directly in a product, without a separate application of an adhesive being needed, as the latter is already present in the adhesive layer of the composite material.

A method for producing a precursor composite material pursuant as outlined above with the following steps is also indicated:

A) Providing a layer sequence, comprising an adhesive layer, a carrier layer on the adhesive layer, a release layer on the carrier layer and a parting layer on the release layer, B) Arranging the side of the adhesive layer facing away from the layer sequence and the side of the parting layer facing away from the layer sequence at least in sub-regions of the layer sequence.

This method allows a precursor composite material to be produced as outlined above. The features indicated with regard to the precursor composite material regarding the layer sequence, the adhesive laxer, the carrier layer, the release layer and the parting layer thus apply analogously to the method. Such a method enables a very rapid production of a precursor composite material and the production of an easy-to-handle precursor composite material of which a composite material can be produced by re-sorting the sequence of the layers.

(Method) Step A) can comprise the following steps:

A1) Coextruding at least the carrier layer and the release layer, and

A2) Coating at least the carrier layer with the adhesive layer.

The coextrusion in step A1) can ensue by means of blown-film extrusion or cast-film extrusion.

The carrier layer and the release layer can be coextruded in step A1) and the carrier layer coated with the adhesive layer and the release layer with the parting layer in step A2). The thickness of the carrier layer and the release layer are configured during the extrusion in step A1). Alternatively, the parting layer, the release layer and the carrier layer can be coextruded in step A1) and the carrier layer coated with the adhesive layer in step A2). In such case, the thickness of the parting layer, the carrier layer and the release layer are configured in step A1), as well as a laminate produced in which the release layer is arranged between the carrier layer and the parting layer. The coating in step A2) always ensues on the side of the adhesive layer facing away from the carrier layer and, if need be, on the side of the parting layer facing away from the release layer.

Step A1) thus allows a very low thickness of the carrier layer and/or the release layer as well as, if need be, of the parting layer to be configured. The subsequent coating and arrangement of the layer sequence enables these thin layers to be further transformed without destruction, as they are not exposed to a tension alone, and instead only in a laminate of layers.

When the carrier layer and the release layer are coextruded in step A1), a coating of the release layer with the parting layer can ensue in step A2), wherein the material of the parting layer is silicone. If the parting layer is already extruded with the carrier layer and the release layer in step A1), hardened polysiloxane and thermoplastic silicone elastomer can be selected as material for the parting layer.

The coextruded layers in the method are thus coated and are subsequently no longer individually subjected to the tension, which influences the layer sequence in the following further transformation process.

The layer sequence can be wound in step B). During a winding the side of the adhesive layer facing away from the layer sequence and the side of the parting layer facing away from the layer sequence can be arranged on top of each other, at least in sub-regions. Such an arrangement makes the delamination of the carrier layer and of the release layer needed to make a composite material out of the precursor composite material particularly easy to realize.

Furthermore, a method for producing the above-described composite material is provided, which comprises a release layer, a parting layer on the release layer, an adhesive layer on the parting layer and a carrier layer on the adhesive layer. The method comprises the following steps:

C) Producing a precursor composite material using a method as described above, and D) Delaminating the carrier layer and the release layer of the precursor composite material.

This thus allows a composite material to be produced particularly easily from the above-described precursor composite material, in which the carrier layer and the release layer of the precursor composite material are delaminated. The bond between adhesive layer and parting layer remains simultaneously preserved, and therefore a rearrangement of the layer sequence of the precursor composite material ensues and the composite material results. The production of the composite material thus ensues by using the precursor composite material and rearranging the layers of the precursor composite material.

This method thus provides a composite material, which can be used as such for producing sanitary towels, pantiliners, incontinence products, labels and stickers, for example, without a separate adhesive film needing to be produced.

Furthermore, the use of a precursor composite material as outlined above for producing a composite material is provided. A precursor composite material as described above can thus be used to produce a composite material with the above-stated properties. In particular, this results in improved composite material properties.

Furthermore, the use of the composite material with the above-stated properties as label, sticker or as component in a hygienic laminate is provided. Label, sticker or hygienic laminate can, for example, have advantageous properties, due to the particularly thin release and/or carrier layer that are realisable in the precursor composite material.

Further advantages, advantageous embodiments and developments result in the following in connection with the embodiments described by the illustrations.

Figure 3:
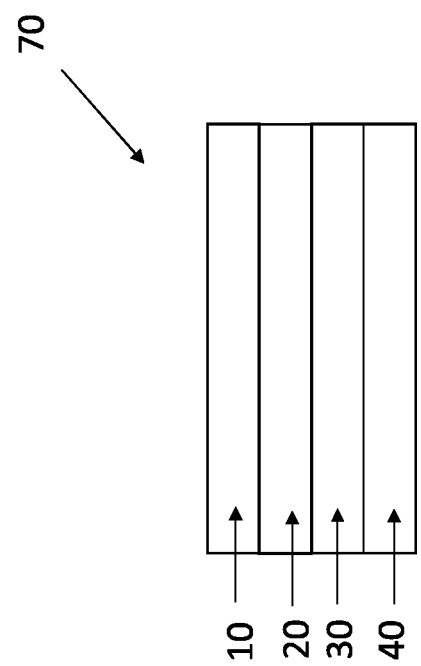
Figure 4C:
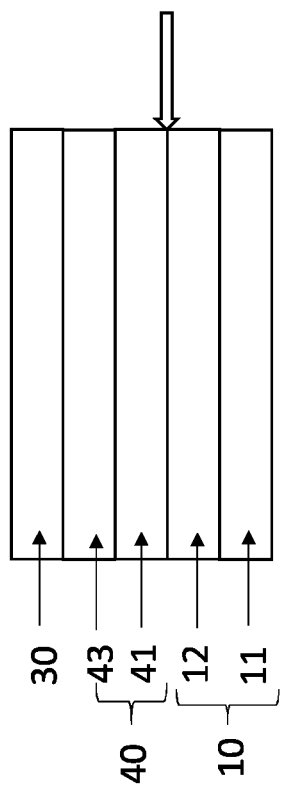
Figure 5C:
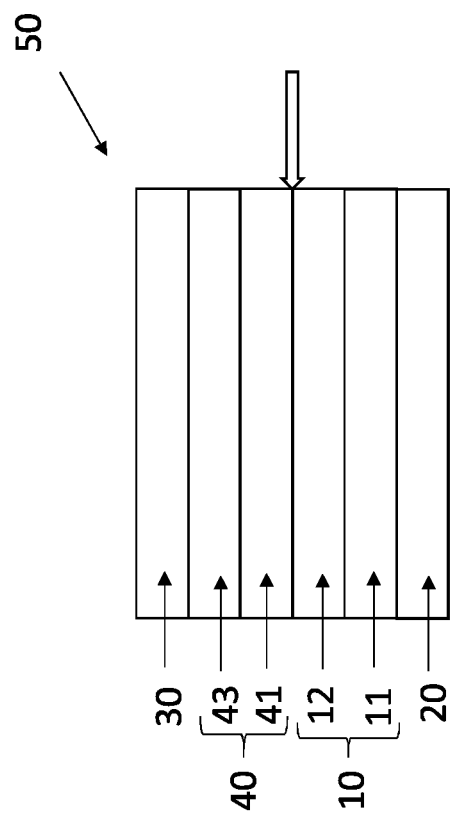
Figure 6C:
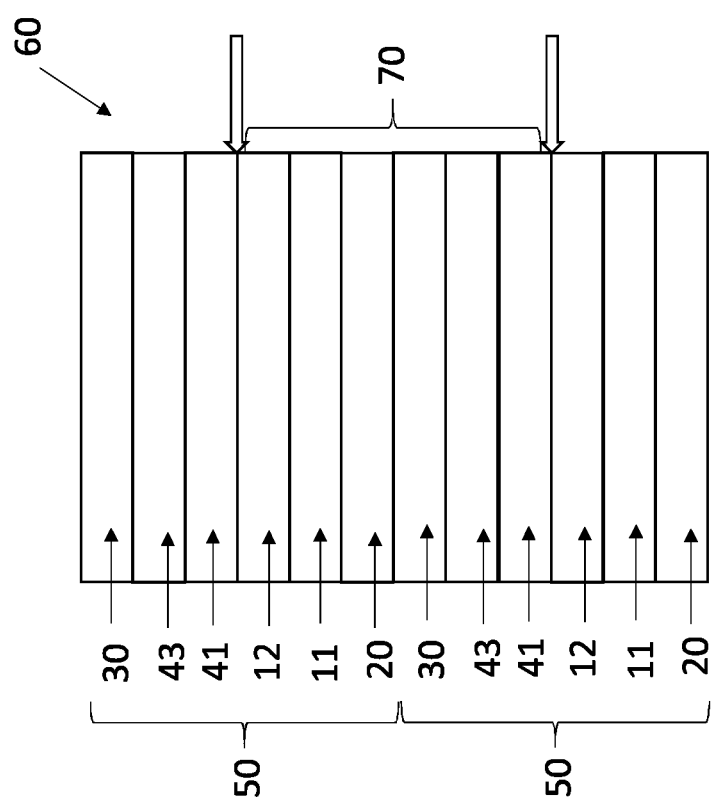

FIGS. 1a and 1b show schematic side views of a precursor composite material pursuant to one embodiment, FIG. 2 shows the schematic side view of a precursor composite material pursuant to a further embodiment, FIG. 3 shows the schematic side view of a composite material, FIGS. 4a, 4b and 4c show schematic side views of coextruded layers of the precursor composite material, FIGS. 5a, 5b and 5c show schematic side views of layer sequences of the precursor composite material pursuant to various embodiments, FIGS. 6a, 6b and 6c show schematic side views of precursor composite materials pursuant to various embodiments, FIGS. 7a and 7b show schematic side views of the method for producing a composite material using the precursor composite material, FIGS. 8a and 8b show the schematic side view and schematic top view of a hygienic laminate.

Identical, similar or seemingly identical elements in the embodiments can each be furnished with the same reference numerals. The elements shown and the size ratios thereof relative to each other should not be viewed as true-to-scale; instead individual elements, such as layers and areas, for example, can be shown exaggeratedly large for the sake of better representation or better understanding.

FIGS. 1a and 1b show schematic side views of a precursor composite material 60. Shown in each case are excerpts of the precursor composite material 60. FIG. 1b shows the layer sequence 50 of the precursor composite material 60, which is present in a wound manner. FIG. 1a also shows the layer sequence 50, which is present in a wound manner, but as cross-section through the winding, and therefore a plurality of layer sequences 50 arranged on top of each other are to be seen. Depending on the size of the winding, many more layer sequences 50 can be present arranged on top of each other in the winding.

Each layer sequence 50 has an adhesive layer 20, a carrier layer 10, a release layer 40 and a parting layer 30. The latter are arranged on top of each other in such a way that they have joint limiting surfaces relative to each other. Due to the arrangement on top of each other, the parting layer 30 and the adhesive layer 20 additionally have a joint limiting surface, at least in sub-regions 25 of the layer sequence.

The materials of the adhesive layer 20 are selected in such a way that the adhesive force between adhesive layer 20 and parting layer 30 is greater than the delamination force between the carrier layer and the release layer 40. The material of the adhesive layer 20 is a pressure-sensitive adhesive that remains permanently adhesive and/or highly viscous once applied to the carrier layer. The material of the parting layer 30 can be silicone, hardened polysiloxane or a thermoplastic silicone elastomer. The carrier layer 10 can comprise polyethylene, polypropylene, polypropylene copolymers of thermoplastic elastomers. The release layer 40 has, for example, polyethylene, polypropylene, polyamide, thermoplastic elastomers, polystyrene, polystyrene copolymers, polyester and/or polyester copolymers as material.

The thickness of the carrier layer 10 equals less than 20 μm, preferably less than 15 μm, more preferably less than 10 μm, most preferably less than 5 μm. The thickness of the release layer 40 equals less than 40 μm, preferably less than 30 μm, more preferably less than 20 μm and most preferably less than 15 μm.

For example, the adhesive layer 20 is made out of the pressure-sensitive adhesive Solucryl 147 produced by Henkel (an acrylic copolymer), the carrier layer 10 of a polyether copolymer-based TPE-U Pearlthane Clear 15N85 produced by Merquinsa, the release layer 40 of the low-density polyethylene Lupolen 2420 F produced by LyondellBasell and the parting layer 30 of a silicone based on Tego RC 902 (98%) and Tego Photoinitiator A 18 (2%) produced by EVONIK.

FIG. 2 shows a further embodiment of the precursor composite material 60 in schematic side view. This illustration should also be understood as a section of a precursor composite material 60 in which two layer sequences 50 arranged on top of each other are to be seen. Depending on the arrangement of the precursor composite material or thickness of the winding of the precursor composite material 60, a plurality of layer sequences 50 can also be arranged on top of each other.

The carrier layer 10 in this example contains two partial layers in each case, a first carrier layer 11 and a second carrier layer 12. The first carrier layer 11 can comprise a polymer, such as polyethylene, polypropylene, polypropylene copolymers, thermoplastic elastomers or combinations thereof. The second carrier layer 12 can comprise a polyethylene, polypropylene, polypropylene copolymers as well as thermoplastic elastomers and combinations thereof. The combination of a plurality of carrier layers serves to configure the softness of the carrier layer. This can, for example, be of relevance when the carrier layer in a hygienic laminate has the function of an underwear-protecting film, which needs to be soft when used. If a thermoplastic elastomer, TPE-E or TPE-U for example, is used as material for the carrier layers, the carrier layer is also breathable.

Furthermore, the release layer 40 is subdivided into three partial layers and comprises the first release layer 41, the second release layer 42 as well as the third release layer 43. The first release layer 41 has, for example, a polymer selected from a group comprising polyethylene, polypropylene, polyamide, thermoplastic elastomers, polystyrene, polystyrene copolymers, polyester and polyester copolymers. The second release layer 42 comprises a polymer serving as an adhesion promoter. The third release layer 43 can in turn comprise, for example, polymers, such as polyethylene or polyolefins. The subdivision of the release layer 40 into three partial layers serves to modify the stiffness or softness of the release layer 40. In addition, when polyamide is used as material for the release layer 40, the costs of the release layer can be reduced, in that the expensive polyamide is replaced by the sequence polyolefin/adhesion promotor/polyamide. The thicknesses of the carrier layer 10 and of the release layer 40 are equivalent to the thicknesses as stated with regard to FIGS. 1a and 1b.

When using the precursor composite material or when using the composite material produced from the precursor composite material, the parting layer 30 serves as protective coating of the adhesive layer 30 and enables simple removal. The adhesive layer 20 can thus be adhered when used on an application surface, such as textiles, for example.

The adhesive layer 20 in an exemplary structure is made out of the pressure-sensitive adhesive Solucryl 147 produced by Henkel, the carrier layer 10 of the high-density polyethylene Hostalen GF 9045 F produced by LyondellBasell, the parting layer 30 of a silicone on the basis of Tego RC 902 (98%) and Tego Photoinitiator A 18 (2%) produced by EVONIK and the release layer 40 of three partial layers, wherein the first release layer 41 is made out of the polyamide Durethan C 38 F produced by Lanxess in a thickness of 1 μm to 10 μm, the second release layer 42 of the adhesion-promoting homopolypropylene-based polymer Admer QB 520 E produced by Mitsui Chemicals in a thickness of 1 μm to 10 μm and the third release layer 43 of a polyolefin or high-density polyethylene, such as Hostalen GF 9045 F, produced by LyondellBasell in a thickness of 1 μm to 30 μm.

FIG. 3 shows the schematic side view of a composite material 70. The latter comprises a release layer 40, a parting layer 30 on the release layer 40, an adhesive layer 20 on the parting layer as well as a carrier layer 10 on the adhesive layer 20. Such a composite material 70 is produced from the precursor composite material 60, and therefore the materials and layer thicknesses of the layers indicated with regard to the precursor composite material also apply to the layers of the composite material 70. Thus, above all, the carrier layer 10 and/or the release layer 40 are designed in a particularly thin manner, which makes the composite material 70 suitable for use in a hygienic laminate or as a label, for example.

In particular, the use in a hygienic laminate leads to an improved wearing comfort due to the thin layers 10 and 40.

The following FIGS. 4 to 7 explain the method for producing the precursor composite material 60 as well as the composite material 70 produced from the precursor composite material 60. FIGS. 4 to 6 refer to the production of the precursor composite material 60, FIG. 7 to the production of the composite material 70. Each of FIGS. 4 to 6 shows three embodiments of a precursor composite material 70 or the steps to the production thereof. FIGS. 4a, 5a and 6a refer to a first embodiment, FIGS. 4b, 5b and 6b refer to a second embodiment and FIGS. 4c, 5c and 6c refer to a third embodiment.

FIG. 4 shows schematic side views of coextruded layers of the precursor composite material 60 after step A1). FIG. 4a shows a first embodiment, in which a carrier layer 10 and a release layer 40 are coextruded, FIG. 4b shows a second embodiment, in which the carrier layer 10 is composed of two partial layers and the release layer 40 is composed of three partial layers, and therefore a total of five coextruded layers are present after step A1). The respective materials of the individual layers are equivalent to those stated with regard to FIGS. 1 and 2. FIG. 4c shows a third embodiment, in which a first carrier layer 11 and a second carrier layer 12 as carrier layer 10, a first release layer 41 and a third release layer 43 as release layer 40, as well as a parting layer 30 are coextruded together. In such case, the parting layer 30 comprises a material selected from a hardened polysiloxane and a thermoplastic silicone elastomer. Such materials can be coextruded and thus also designed in a particularly thin manner.

Schematic arrows in all of FIGS. 4a, 4b and 4c show where the controlled delamination for producing a composite material will later take place, i.e. in each case between the carrier layer 10 and the release layer 40, or between the second carrier layer 12 and the first release layer 41. The delamination is rendered possible due to the presence of an adhesive force between the adhesive layer 20 and the parting layer 30, said adhesive force being greater than the delamination force between the carrier layer 10 and the release layer 40.

FIG. 5 shows the schematic side view of layer sequences of various embodiments of the precursor composite material 60. The method for producing the precursor composite material 60 is an intermediate product, which is obtained after step A).

After the coextrusion of the carrier layer 10 and the release layer 40 shown in FIG. 4, during which the thickness of each is configured by tension, at least the carrier layer 10 is coated with an adhesive layer 20 in step A2). In the embodiment pursuant to FIG. 5 the carrier layer 10 is coated with the adhesive layer 20 and the release layer 40 with the parting layer 30. In such case, a silicone layer is used as parting layer 30. In the embodiment pursuant to FIG. 5 the first carrier layer 11 is coated with the adhesive layer 20 and the third release layer 43 also coated with a parting layer 30. In such case, the parting layer 30 is also a silicone layer. In the embodiment pursuant to FIG. 5c the carrier layer 30 has already been coextruded with the release layer 40 and the carrier layer 10, and therefore only one coating of the first carrier layer 11 with the adhesive layer 20 has taken place in step A2). In each case, the coatings preserve layer sequences 50, which can now also be further transformed at a lower thickness than carrier 10 and/or release layer 40, without any destruction of the thin layers occurring. In each of FIGS. 5a to 5c schematic arrows again show where the controlled delamination of the layers occurs during the further transformation of the precursor composite material into a composite material.

FIG. 6 shows schematic side views of the finished precursor composite material 60 of the various embodiments after step B), i.e. after the arrangement of the layer sequence 50, and therefore the side of the adhesive layer 20 facing away from the layer sequence is arranged at least in sections on the side of the parting layer 30 facing away from the layer sequence. Each of the schematic side views of FIGS. 6a to 6c should also be understood as excerpts as, depending on the length and arrangement or winding of the layer sequence, considerably more layer sequences 50 can be arranged on top of each other. The individual layer sequences 50 of FIGS. 6a and 6b have already been explained above with regard to FIGS. 1a and 2. Each of the parting layers 30 is a silicone layer. The layer sequence 50, as shown in FIG. 6c, comprises parting layers 30, which comprise hardened polysiloxane or thermoplastic silicone elastomers as material, the release layer 40 further contains two partial layers, namely the first release layer 41 and the third release layer 43.

The schematic arrows in FIGS. 6a to 6c again show at what point a controlled delamination takes place in the event of the arrangement of the layer sequences 50 being dissolved, i.e. for example, in the event of the layer sequence 50 being unwound. Each illustration indicates at what point a composite material 70 will result in the event of the re-sorting or the delamination of the precursor composite material 60.

FIGS. 7a and 7b shows the method for producing the composite material 70 from the precursor composite material 60 on the basis of a schematic side view of a wound precursor composite material 60. These illustrations should again be understood as excerpts. FIGS. 7a and 7b show the method on the basis of a precursor composite material 60, comprising a parting layer 30, a silicone layer in this case, a release layer 40, a carrier layer 10 as well as an adhesive layer 20. Analogous methods would also be applicable to layer sequences 50 of the precursor composite material 60, which each have a plurality of partial layers as carrier layer 10 and as release layer 40. During the controlled delamination of the precursor composite material 60 the combination of parting layer 30 and release layer 40 is initially unwound alone (FIG. 7a), which is particularly easy to achieve, as the delamination force between the carrier layer 10 and the release layer 40 is less than the adhesive force between the adhesive layer 20 and the parting layer 30 on which the adhesive layer is arranged in sub-regions of the layer sequence 50. As soon as half the layer sequence made up of parting layer 30 and release layer 40 has been unwound and the sub-region of the wound layer sequence in which the parting layer 30 is arranged on the adhesive layer 20 has been reached, the composite material 70, in which carrier layer 10, adhesive layer 20, parting layer 30 and release layer 40 are arranged on top of each other, is unwound, as here too the delamination force between the release layer 40 and the carrier layer 10 is again less than the adhesive force between the adhesive layer 20 and the parting layer 30. This allows the composite material 70 to be acquired from the precursor composite material 60 in a particularly easy manner (FIG. 7b).

FIG. 8 shows the schematic side view (FIG. 8a) and a schematic top view (FIG. 8b) of a hygienic laminate in which a composite material 70, produced from the precursor composite material 60, is used.

In FIG. 8a the composite material 70, consisting of release layer 40, parting layer 30 on the release layer 40, adhesive layer 20 on the parting layer 30 as well as a carrier layer 10 on the adhesive layer 20 is arranged in such a way that further layers of the hygienic laminate are arranged on the carrier layer 10. The latter comprise an adhesion 85, a suction core on the adhesion 85, a distribution layer 83 on the suction core 84, an adhesion 82 on the distribution layer 83 and a non-woven covering 81 on the adhesion 82. In such case, the carrier layer 10 can be designed as an underwear-protecting film. If the hygienic laminate is used by a consumer, the release film 40 can be removed together with the parting layer 30 and the hygienic laminate again removably attached to the adhesive layer 20 in the underwear.

FIG. 8b shows a top view of the hygienic laminate 80 in which only the non-woven covering 81 is visible.

When using the composite material as shown in FIG. 8, it is advantageous when the carrier layer 10 is designed in a breathable manner, which can be achieved by using TPE-U or TPE-E as material for the carrier layer 10.

The invention is not restricted by the description on the basis of the embodiments. Instead, the invention comprises every new feature as well as every combination of features, which in particular includes every combination of features in the claims, even if such claim or such combination is not itself explicitly provided in the claims or embodiments.

LIST OF REFERENCE NUMERALS

10 Carrier layer
11 First carrier layer
12 Second carrier layer
20 Adhesive layer
25 Sub-region of the layer sequence, wherein the parting layer (30) and the adhesive layer (20) have a joint surface.
30 Parting layer
40 Release layer
41 First release layer
42 Second release layer
43 Third release layer
50 Layer sequence
60 Precursor composite material
70 Composite material
80 Hygienic laminate
81 Non-woven covering
82 Adhesion
83 Distribution layer
84 Suction core
85 Adhesion

The invention claimed is:

1. A precursor composite material having a layer sequence, comprising an adhesive layer, a carrier layer on the adhesive layer, a release layer on the carrier layer and a parting layer on the release layer, wherein the layer sequence is wound such that at least a sub-region of the side of the adhesive layer facing away from the layer sequence is arranged on the side of the parting layer facing away from the layer sequence, wherein an adhesive force is present between the adhesive layer and the parting layer, said adhesive force being greater than a delamination force between the carrier layer and the release layer.

2. The precursor composite material according to claim 1, wherein the release layer has a thickness of less than 40 µm and/or the carrier layer has a thickness of less than 20 µm.

3. The precursor composite material according to claim 1, wherein the adhesive layer has a material selected from a group comprising pressure-sensitive adhesives.

4. The precursor composite material according to claim 1, wherein the release layer has a material selected from a group comprising polyamide, polystyrene, thermoplastic elastomers, polystyrene copolymers, polyester, polyester copolymers, polyolefins, combinations thereof and combinations of polyamide, polystyrene, thermoplastic elastomers, polystyrene copolymers, polyesters, polyester copolymers and/or polyolefins with adhesion promotors.

5. The precursor composite material according to claim 1, wherein the carrier layer has a material selected from a group comprising polyolefins, polyolefin copolymers, thermoplastic elastomers and combinations thereof.

6. The precursor composite material according to claim 1, wherein the parting layer has a material selected from a group comprising silicone, hardened polysiloxane and thermoplastic silicone elastomer.

7. A composite material, produced from the precursor composite material according to claim 1, comprising a release layer, a parting layer on the release layer, an adhesive layer on the parting layer and a carrier layer on the adhesive layer.

8. A method for producing the composite material according to claim 7 comprising the steps:
A) Providing a layer sequence, comprising an adhesive layer, a carrier layer on the adhesive layer, a release layer on the carrier layer and a parting layer on the release layer;
B) Winding the layer sequence such that at least a sub-region of the side of the adhesive layer facing away from the layer sequence and the side of the parting layer facing away from the layer sequence to produce a precursor composite material; and
C) Delaminating the carrier layer and the release layer of the precursor composite material to produce a composite material.

9. A method for producing the precursor composite material according to claim 1, comprising the steps:
A) Providing a layer sequence, comprising an adhesive layer, a carrier layer on the adhesive layer, a release layer on the carrier layer and a parting layer on the release layer; and
B) Winding the layer sequence such that at least a sub-region of the side of the adhesive layer facing away from the layer sequence is arranged on the side of the parting layer facing away from the layer sequence.

10. The method according to claim 9, wherein step A) comprises the steps:
A1) Coextruding at least the carrier layer and the release layer; and
A2) Coating at least the carrier layer with the adhesive layer.

11. The method according to claim 10, wherein the carrier layer and the release layer are coextruded in step A1) and the carrier layer is coated with the adhesive layer and the release layer with the parting layer in step A2), or wherein the parting layer, the release layer and the carrier layer are coextruded in step A1) and the carrier layer is coated with the adhesive layer in step A2).

12. A label, sticker or a component in a hygienic laminate, comprising a composite material of claim 7.

* * * * *